US012558681B2

(12) United States Patent
Liu et al.

(10) Patent No.: US 12,558,681 B2
(45) **Date of Patent: *Feb. 24, 2026**

(54) METHOD FOR IMPROVING STABILITY OF CATALYST IN RECYCLING HFC-23

(71) Applicants: Zhejiang Research Institute of Chemical Industry Co., Ltd., Hangzhou Zhejiang (CN); Zhejiang Lantian Environmental Protection Hi-Tech Co., Ltd., Hangzhou (CN); Sinochem Lantian Co., Ltd., Hangzhou (CN)

(72) Inventors: Wucan Liu, Zhejiang (CN); Jianjun Zhang, Zhejiang (CN); Wenfeng Han, Zhejiang (CN); Shucheng Wang, Zhejiang (CN); Feixiang Zhou, Zhejiang (CN)

(73) Assignees: Zhejiang Research Institute of Chemical Industry Co., Ltd., Zhejiang (CN); Zhejiang Lantian Environmental Protection Hi-Tech Co., Ltd., Hangzhou (CN); Sinochem Lantian Co., Ltd., Hangzhou (CN)

( * ) Notice: Subject to any disclaimer, the term of this patent is extended or adjusted under 35 U.S.C. 154(b) by 1103 days.

This patent is subject to a terminal disclaimer.

(21) Appl. No.: 17/427,523

(22) PCT Filed: Feb. 24, 2020

(86) PCT No.: PCT/CN2020/076372
§ 371 (c)(1),
(2) Date: Jul. 30, 2021

(87) PCT Pub. No.: WO2021/114481
PCT Pub. Date: Jun. 17, 2021

(65) Prior Publication Data
US 2022/0105504 A1        Apr. 7, 2022

(30) Foreign Application Priority Data
Dec. 13, 2019        (CN) .......................... 201911281818.4

(51) Int. Cl.
*B01J 23/94*        (2006.01)
*B01J 23/86*        (2006.01)
*B01J 38/04*        (2006.01)
*C07C 17/20*        (2006.01)

(52) U.S. Cl.
CPC ............. *B01J 38/04* (2013.01); *B01J 23/862* (2013.01); *B01J 23/864* (2013.01); *B01J 23/866* (2013.01); *B01J 23/94* (2013.01); *C07C 17/202* (2013.01)

(58) Field of Classification Search
CPC ...... B01J 23/862; B01J 23/864; B01J 23/866; B01J 23/94; B01J 38/04; C07C 17/202
See application file for complete search history.

(56) References Cited

U.S. PATENT DOCUMENTS

| | | | |
|---|---|---|---|
| 3,009,966 | A | 11/1961 | Murray |
| 2003/0166981 | A1 | 9/2003 | Gelblum |

FOREIGN PATENT DOCUMENTS

| | | |
|---|---|---|
| CN | 103467239 A | 12/2013 |
| CN | 104628513 A | 5/2015 |
| CN | 104628514 A | 5/2015 |
| CN | 109748775 A | 5/2019 |
| DE | 231341 A1 | 12/1985 |
| EP | 1148039 A1 | 10/2001 |
| WO | WO9629296 A1 | 9/1996 |

OTHER PUBLICATIONS

Han et al (CN104628513, machine translation), 2015.*

* cited by examiner

*Primary Examiner* — Smita S Patel
(74) *Attorney, Agent, or Firm* — Muncy, Geissler, Olds & Lowe, P.C.

(57)        ABSTRACT

A method for improving the stability of a catalyst in recycling HFC-23 is provided. The recycling is realized by means of a fluorine-chlorine exchange reaction with HFC-23 and a halogenated hydrocarbon. The catalyst for the fluorine-chlorine exchange reaction comprises a main body catalyst and a metal oxide, wherein the metal oxide is selected from at least one metal oxide of K, Na, Fe, Co, Cu, Ni, Zn or Ti, and has an addition amount of 0.1-5 wt %. The method has advantages such as a good catalyst stability, a long life, and a low content of by-product CFC-12.

8 Claims, No Drawings

METHOD FOR IMPROVING STABILITY OF CATALYST IN RECYCLING HFC-23

TECHNICAL FIELD

The present invention relates to HFC-23 recycling, particularly to a method for improving the stability of a catalyst and suppressing the selectivity of the by-product CFC-12 in recycling HFC-23.

BACKGROUND

HFC-23 ($CHF_3$, trifluoromethane, R23) is an inevitable by-product in the industrial production of HFC-22 (HCFC-22, monochlorodifluoromethane, R22 or $CHClF_2$), has a strong greenhouse effect, with a Global Warming Potential (GWP) value of 14,800 times that of $CO_2$. According to statistics, in 2013, HFC-23 emissions in China accounted for 68% of the world's emissions, with a production volume of more than 20,000 tons, equivalent to an annual $CO_2$ emission of 296 million tons. Therefore, HFC-23 recycling is an important issue in realizing energy saving and emission reduction.

At present, HFC-23, a by-product produced in the production process of HCFC-22, is generally discharged directly or disposed by high-temperature incineration at 1200° C. However, direct discharge will cause environmental pollution, and high-temperature incineration at 1200° C. will require high operation and equipment cost, which will increase the production cost of HCFC-22. In view of this, in the prior art, the following methods are adopted for the recycling of HFC-23.

U.S. Pat. No. 3,009,966A discloses a method for preparing TFE and hexafluoropropylene (HFP) by pyrolysis of trifluoromethane at 700-1090° C. However, this method produces more by-product perfluoroisobutylene (PFIB); even at the cost of lowering the yield, a non-negligible amount of PFIB will be produced at a low temperature, while PFIB has extremely high toxicity and its treatment process is more complicated.

WO96/29296A discloses a method for co-cracking HCFC-22 and HFC-23 to form macromolecular fluoroalkanes. Although the conversion rate of HCFC-22 can reach 100% in this method, the yield of the product pentafluoroethane is only 60%, and additional low-value by-products that need treatment or disposal are produced.

U.S. patent US2003/0166981 discloses that HFC-23 and HCFC-22 are pyrolyzed to produce a mixture of pentafluoroethane (HFC-125), heptafluoropropane (HFC-227ea), TFE and HFP at a temperature of 690-775° C. using gold as a catalyst. However, this method has a high pyrolysis temperature and harsh reaction conditions.

Chinese patent CN104628514A discloses that methane and trifluoromethane are introduced into a reactor equipped with a catalyst at a certain ratio, and 02 is added at the same time to react under higher temperature conditions, to generate vinylidene fluoride (VDF). However, this route is also a cracking route, with high pyrolysis temperature and harsh reaction conditions.

Chinese patent CN104628513A discloses a method for converting trifluoromethane and chloroform as raw materials into HCFC-22 under the catalysis of Lewis acid. This method realizes the conversion of trifluoromethane at a relatively low temperature (below 400° C.) through intermolecular fluorine-chlorine exchange. However, this method uses a strong Lewis acid catalyst, which has poor stability and is very prone to deactivation due to carbon deposition and sintering.

Chinese patent CN109748775A discloses that, in the presence of $MgF_2$, $Al_2O_3$, partially fluorinated alumina or $AlF_3$ catalysts, trifluoromethane and dichloromethane are reacted and converted into difluoromethane with a higher value, and at the same time, $Cl_2$, $CCl_4$, $H_2$, $O_2$, $CO_2$, $O_3$ and nitrogen oxide promoting gas are continuously added in the reaction stage, to enhance the catalytic efficiency and stability of the catalyst. However, in this method, the selectivity of the by-product CFC-12 is significantly increased, reaching 2% to 8%, while the product selectivity is low.

SUMMARY

In order to solve the foregoing technical problems, the present invention provides a method for simultaneously improving the stability and life of the catalyst and controlling the content of the by-product CFC-12.

The object of the present invention is achieved through the following technical solutions:

A method for improving the stability of a catalyst in recycling HFC-23, the recycling is realized by means of a fluorine-chlorine exchange reaction with HFC-23 and a halogenated hydrocarbon:

$$CHF_3+CH(Cat.\ CHCH^+_2)+CHClF_2F$$

The above fluorine-chlorine exchange products include monochlorodifluoromethane (HCFC-22) and dichlorofluoromethane (HCFC-21). The inventors found that the two products are prone to disproportionation reactions on the surface of the catalyst. The reaction formula is as follows:

$$2CHClF_2 \rightarrow CHF_3+CHFCl_2$$

$$2CHCl_2F \rightarrow CHCl_3+CHClF_2$$

In order to achieve rapid desorption of the products HCFC-22 and HCFC-21 on the surface of the catalyst, reduce the carbon deposition on the surface of the catalyst and improve the stability and life of the catalyst, the following technical solutions are adopted.

The catalyst comprises a main body catalyst and a metal oxide, and the metal oxide is selected from at least one metal oxide of K, Na, Fe, Co, Cu, Ni, Zn or Ti, and has an addition amount of 0.1-5 wt %. The addition method is a conventional method for preparing the existing catalyst, such as, physical grinding with the main body catalyst, or incorporation by the metal salt solution precursor wet mixing method or dipping method and then calcination. Preferably, the metal oxide is selected from a metal oxide of Fe, Co, Ni or Zn, and has an addition amount of 0.5-2 wt %.

The main body catalyst is chromium, aluminum, or magnesium-based catalyst or chromium, aluminum, or magnesium catalyst supported on activated carbon/graphite; preferably, the main body catalyst is selected from at least one of $Cr_2O_3$, $Cr_2O_3/Al_2O_3$, $Cr_2O_3/AlF_3$, $Cr_2O_3/C$, MgO, MgO/$Al_2O_3$, MgO/AlF_3, MgO/AlF_3, $Al_2O_3$ or $AlF_3$.

The halogenated hydrocarbon in the fluorine-chlorine exchange reaction is chloroform or a mixture containing chloroform. The conditions of the fluorine-chlorine exchange reaction are: molar ratio of HFC-23 to halogenated hydrocarbon of 1:1-3, a reaction temperature of 250-400° C., a reaction pressure of 0.1-3 bar, and a residence time of 4-50 s. Preferably, a molar ratio of HFC-23 to halogenated hydrocarbon of 1:1.2-2.2, a reaction temperature of 300-360° C., a reaction pressure of 1-2 bar, and a residence time of 4-12 s.

In order to further improve the stability of the catalyst and suppress the content of by-product CFC-12, the selectivity of HCFC-22 in the process of fluorine-chlorine exchange reaction is monitored, and a decarbonization gas is introduced to maintain the selectivity of HCFC-22 at 50%-55% when the selectivity of HCFC-22 drops to 46%-48%.

The decarbonization gas is introduced through the catalyst bed and can react with the carbon deposition on the catalyst surface to generate gaseous substances, thereby achieving the purpose of eliminating the catalyst carbon deposition and improving the stability and life of the catalyst. The decarbonization gas is a mixed gas of at least one of air, $Cl_2$, $CO_2$, or $O_2$ with $N_2$.

Further, the decarbonization gas, HFC-23, and halogenated hydrocarbon form a mixed gas before introduction, when the selectivity of HCFC-22 drops to 46%-48%, the decarbonization gas with a volume content of 0.5n % of the mixed gas is introduced for a duration of 10n hours, n is the number of times of regenerations, and n is ≤6.

Specifically, when the selectivity of HCFC-22 drops to 46%-48%, 0.5% of decarbonization gas is introduced for 10 hours, and the selectivity of HCFC-22 is gradually restored to 50%-55%; when the selectivity of HCFC-22 drops for a second time, 1% decarbonization gas is introduced for 20 hours, and the selectivity of HCFC-22 gradually recovers; when the selectivity of HCFC-22 drops for a third time, 1.5% decarbonization gas is introduced for 30 hours, and the selectivity of HCFC-22 gradually recovers. And so on, until n=6. When the number of times of regenerations n is ≤6, the carbon removal effect is ideal, the selectivity of HCFC-22 is basically maintained at 50%-55%, the selectivity of by-product CFC-12 is less than 1%, and the catalyst maintains a good stability. When the number of times of regenerations n is >6, the selectivity of HCFC-22 shows a trend of accelerated decline. At this time, the decarbonization gas with a volume content of 1%-3% of the mixed gas is continuously introduced to maintain a good stability of the catalyst.

During intermittent or continuous introduction of decarbonization gas, the raw materials HFC-23 and halogenated hydrocarbon are fed normally.

Compared with the prior art, the present invention has the following beneficial effects.

(1) By adding metal oxide to the catalyst, the present invention accelerates the desorption of the products HCFC-22 and HCFC-21 on the surface of the catalyst, thereby inhibiting the disproportionation reaction on the surface of the catalyst, reducing the carbon deposition caused by side reactions and improving the stability and life of the catalyst;

(2) By monitoring the selectivity of HCFC-22, the present invention adjusts the timing of introducing decarbonization gas, which not only improves the stability of the catalyst, but also controls the selectivity of by-product CFC-12 to be less than 1%, thereby enhancing the product selectivity, suitable for industrial production.

DETAILED DESCRIPTION

The present invention will be further described below in conjunction with specific examples, but the present invention is not limited to these specific embodiments. Those skilled in the art should realize that the present invention covers all alternatives, improvements and equivalents that may be included in the scope of the claims.

Example 1

Preparation of catalyst: Chromium trioxide and cobalt trioxide powder were ground and mixed, and the Co mass content was controlled to 1.0% to obtain 1.0% $Co/Cr_2O_3$ catalyst precursor. The 1.0% $Co/Cr_2O_3$ catalyst precursor was subjected to two-stage fluorination treatment: 1) fluorination treatment was performed at 250° C. for 2 hours under a mixed atmosphere of 10% hydrogen fluoride and 90% nitrogen; 2) fluorination treatment was performed at 300° C. for 5 hours under a hydrogen fluoride atmosphere. A catalyst was obtained after fluorination treatment, which was designated as catalyst 1.

HFC-23 recycling: Trifluoromethane and chloroform were introduced into a reactor containing 50 ml of catalyst 1 at a molar ratio of 1:1.5, and the reaction was carried out under the conditions of a reaction temperature of 310° C., a pressure of 1 bar and a residence time of 5 s. The conversion rate of trifluoromethane was 26.6%, the selectivity of HCFC-22 was 44.8%, the selectivity of HCFC-21 was 54.7%, and the selectivity of by-product CFC-12 was 0.5%. The catalyst was significantly deactivated after 973 h.

Example 2

Preparation of catalyst: Chromium trioxide and iron trioxide powder were ground and mixed, and the Fe mass content was controlled to 1.0% to obtain 1.0% $Fe/Cr_2O_3$ catalyst precursor. The 1.0% $Fe/Cr_2O_3$ catalyst precursor was subjected to two-stage fluorination treatment: 1) fluorination treatment was performed at 250° C. for 2 hours under a mixed atmosphere of 10% hydrogen fluoride and 90% nitrogen; 2) fluorination treatment was performed at 300° C. for 5 hours under a hydrogen fluoride atmosphere. A catalyst was obtained after fluorination treatment, which was designated as catalyst 2.

HFC-23 recycling: Trifluoromethane and chloroform were introduced into a reactor containing 50 ml of catalyst 2 at a molar ratio of 1:1.5, and the reaction was carried out under the conditions of a reaction temperature of 310° C., a pressure of 1 bar and a residence time of 5 s. The conversion rate of trifluoromethane was 26.3%, the selectivity of HCFC-22 was 44.9%, the selectivity of HCFC-21 was 54.5%, and the selectivity of by-product CFC-12 was 0.6%. The catalyst was significantly deactivated after 861 h.

Example 3

Preparation of catalyst: Chromium trioxide and nickel trioxide powder were ground and mixed, and the Ni mass content was controlled to 1.0% to obtain 1.0% $Ni/Cr_2O_3$ catalyst precursor. The 1.0% $Ni/Cr_2O_3$ catalyst precursor was subjected to two-stage fluorination treatment: 1) fluorination treatment was performed at 250° C. for 2 hours under a mixed atmosphere of 10% hydrogen fluoride and 90% nitrogen; 2) fluorination treatment was performed at 300° C. for 5 hours under a hydrogen fluoride atmosphere. A catalyst was obtained after fluorination treatment, which was designated as catalyst 3.

HFC-23 recycling: Trifluoromethane and chloroform were introduced into a reactor containing 50 ml of catalyst 3 at a molar ratio of 1:1.5, and the reaction was carried out under the conditions of a reaction temperature of 310° C., a pressure of 1 bar and a residence time of 5 s. The conversion rate of trifluoromethane was 25.3%, the selectivity of HCFC-22 was 43.8%, the selectivity of HCFC-21 was 55.5%, and the selectivity of by-product CFC-12 was 0.7%. The catalyst was significantly deactivated after 758 h.

Example 4

The operation procedure of this embodiment were the same as that of Example 1, except that the intermittent decarbonization gas was added during the HFC-23 recycling, to burn carbon. The timing of the intermittent introduction of carbon-burning gas: when the selectivity of monochlorodifluoromethane dropped to 46.0% after reaction for 551h, the introduction of raw materials was stopped, and 0.5 wt % (accounting for the total flow of trifluoromethane and chloroform) $O_2$ was introduced for carbon burning for 10 h for the first time. After continuous introduction of raw materials for a period of time, the selectivity of R22 gradually recovered to 54.1%, and when reaction for 952h, the selectivity of R22 dropped to 46.0%; the reaction was stopped immediately, 1.0 wt % $O_2$ was introduced for carbon burning for 20 h for the second time. After the end of carbon burning, raw materials were introduced to react, and the selectivity of R22 gradually recovered to 53.2%, and then dropped to 46.0% at 1304 h; the reaction was stopped immediately and 1.5 wt % 02 was introduced for carbon burning for 30 h for the third time, raw materials were introduced continuously to react, the selectivity of R22 gradually recovered to 52.6% and dropped to 46.0% at 1605h; The reaction was stopped immediately, and 2.0 wt % $O_2$ was introduced for carbon burning for 40 h for the fourth time, the raw materials were introduced continuously to react, and the selectivity of R22 gradually recovered to 51.9%, dropped to 46.0% at 1856h; the reaction was stopped immediately, and 2.5 wt % $O_2$ was introduced for carbon burning for 50 h for the fourth time, the raw materials were introduced continuously to react, and the selectivity of R22 gradually recovered to 51.1%, and dropped to 46.0% at 2057h; the reaction was stopped immediately, and 3.0 wt % $O_2$ was introduced for carbon burning for 60 h for the fourth time, the raw materials were introduced continuously to react, and the selectivity of R22 gradually recovered to 50.6%, and dropped to 46.0% at 2210 h; When 3.0 wt % 02 was mixed in the raw materials to react continuously until 2507 h, the conversion rate of trifluoromethane dropped to 16.6%, and the selectivity of monochlorodifluoromethane dropped to 27.2%. The catalyst was deactivated after reaction for 2507 h, and the conversion rate of trifluoromethane was 25.1%, the selectivity of HCFC-22 was 43.3%, the selectivity of HCFC-21 was 55.4% and the selectivity of the by-product CFC-12 was 0.9%. The tail gas contained trace amount of $CH_4$ and other gases.

The experimental results showed that, after intermittent introduction of appropriate amount of $O_2$ for carbon burning for a reasonable time for more than 6 times, and continuous introduction of $O_2$ for carbon burning, the stability and life of the catalyst were significantly improved, and the selectivity of the by-product CFC-12 was guaranteed to be below 1.0%.

Example 5

The operation procedure of this example was the same as that Example 2, except for the difference that, when the catalyst reacted for 411 h, the selectivity of R22 dropped to 46.0%. After six times of intermittent carbon burning and continuous introduction of carbon-burning gas, the catalyst continued to react until 1945 h and the catalyst was in an inactive state. The conversion rate of trifluoromethane was 24.9%, the selectivity of HCFC-22 was 43.6%, the selectivity of HCFC-21 was 55.5%, the selectivity of by-product CFC-12 was 0.9%. The tail gas contained trace amount of $CH_4$ and other gases.

Example 6

The operation procedure of this example was the same as that Example 2, except for the difference that, when the catalyst reacted for 386 h, the selectivity of R22 dropped to 46.0%. After six times of intermittent carbon burning and continuous introduction of carbon-burning gas, the catalyst continued to react until 1623 h and the catalyst was in an inactive state. The conversion rate of trifluoromethane was 24.7%, the selectivity of HCFC-22 was 42.8%, the selectivity of HCFC-21 was 55.9%, the selectivity of by-product CFC-12 was 1.0%. The tail gas contained trace amount of $CH_4$ and other gases.

Example 7

The operation procedure of this example was the same as that Example 1, except for the difference that, the Co mass content dropped 1.0% to 0.5%. The prepared catalyst was subjected to fluorine-chlorine exchange reaction. After reaction, the conversion of trifluoromethane was 26.5%, the selectivity of HCFC-22 was 44.6%, the selectivity of HCFC-21 was 54.8%, and the selectivity of by-product CFC-12 was 0.6%. The catalyst was significantly deactivated after 654 h.

Example 8

The operation procedure of this example was the same as that Example 1, except for the difference that, the Co mass content increased from 1.0% to 2.0%. The prepared catalyst was subjected to fluorine-chlorine exchange reaction. After reaction, the conversion of trifluoromethane was 26.7%, the selectivity of HCFC-22 was 44.5%, the selectivity of HCFC-21 was 54.8%, and the selectivity of by-product CFC-12 was 0.5%. The catalyst was significantly deactivated after 756 h.

Example 9

The operation procedure of this example was the same as that Example 1, except for the difference that, the molar ratio of trifluoromethane to chloroform was changed from 1:1.5 to 1:1. After reaction, the conversion of trifluoromethane was 24.7%, the selectivity of HCFC-22 was 43.6%, the selectivity of HCFC-21 was 55.6%, and the selectivity of by-product CFC-12 was 0.7%. The catalyst was significantly deactivated after 507 h.

Example 10

The operation procedure of this example was the same as that Example 1, except for the difference that, the molar ratio of trifluoromethane to chloroform was changed from 1:1.5 to 1:2. After reaction, the conversion of trifluoromethane was 25.5%, the selectivity of HCFC-22 was 43.3%, the selectivity of HCFC-21 was 55.8%, and the selectivity of by-product CFC-12 was 0.9%. The catalyst was significantly deactivated after 486 h.

Comparative Example 1

Preparation of catalyst: The chromium trioxide catalyst was subjected to two-stage fluorination treatment: 1) fluorination treatment was performed at 250° C. for 2 hours under a mixed atmosphere of 10% hydrogen fluoride and 90% nitrogen; 2) fluorination treatment was performed at 300° C. for 5 hours under a hydrogen fluoride atmosphere. A catalyst was obtained after fluorination treatment, which was designated as catalyst D1.

HFC-23 recycling: Trifluoromethane and chloroform were introduced into a reactor containing 50 ml of catalyst D1 at a molar ratio of 1:1.5, and the reaction was carried out under the conditions of a reaction temperature of 310° C., a pressure of 1 bar and a residence time of 5 s. The conversion rate of trifluoromethane was 25.6%, the selectivity of HCFC-22 was 44.4%, the selectivity of HCFC-21 54.2%, and the selectivity of by-product CFC-12 was 1.4%. The catalyst was significantly deactivated after 340 h. After taken out, the catalyst was found to become obviously black, and serious carbon deposition occurred.

Comparative Example 2

Preparation of catalyst: Chromium trioxide and calcium oxide powder were ground and mixed, and the Ca mass content was controlled to 1.0% to obtain 1.0% $Ca/Cr_2O_3$ catalyst precursor. The 1.0% $Ca/Cr_2O_3$ catalyst precursor was subjected to two-stage fluorination treatment: 1) fluorination treatment was performed at 250° C. for 2 hours under a mixed atmosphere of 10% hydrogen fluoride and 90% nitrogen; 2) fluorination treatment was performed at 300° C. for 5 hours under a hydrogen fluoride atmosphere. A catalyst was obtained after fluorination treatment, which was designated as catalyst D2.

HFC-23 recycling: Trifluoromethane and chloroform were introduced into a reactor containing 50 ml of catalyst D2 at a molar ratio of 1:1.5, and the reaction was carried out under the conditions of a reaction temperature of 310° C., a pressure of 1 bar and a residence time of 5 s. The conversion rate of trifluoromethane was 26.6%, the selectivity of HCFC-22 was 44.3%, the selectivity of HCFC-21 was 54.7%, and the selectivity of by-product CFC-12 was 1%. The catalyst was significantly deactivated after 345 h, and the addition of Ca element did not increase the life of the catalyst.

Comparative Example 3

The operation procedure of this example was the same as that Example 2, except for the difference that, the raw material gas was continuously mixed with 3.0 wt % $O_2$ and introduced into the bed for reaction. The conversion rate of trifluoromethane was 26.3%, the selectivity of HCFC-22 was 41.5%, the selectivity of HCFC-21 was 55.0%, the selectivity of by-product CFC-12 was 3.5%. The tail gas contained trace amount of $CH_4$ and other gases. The catalyst was significantly deactivated after 341h. The continuous introduction of 3.0 wt % 02 with the raw materials would increase the selectivity of the by-product CFC-12.

The invention claimed is:

1. A method for improving stability of a catalyst in recycling HFC-23 ($CHF_3$, trifluoromethane, R23), the recycling is realized by means of a fluorine-chlorine exchange reaction with HFC-23 and a halogenated hydrocarbon, wherein the catalyst for the fluorine-chlorine exchange reaction comprises a main body catalyst and a metal oxide, and the metal oxide is selected from at least one metal oxide of K, Na, Fe, Co, Cu, Ni, Zn or Ti in an amount of 0.1-5 wt %,
  wherein the fluorine-chlorine exchange reaction comprises monochlorodifluoromethane (HCFC-22) and dischlorofluoromethane (HCFC-21), and
  wherein a selectivity of HCFC-22 in a process of fluorine-chlorine exchange reaction is monitored, and a decarbonization gas is introduced to maintain the selectivity of HCFC-22 at 50%-54% when the selectivity of HCFC-22 drops to 46%-48%.

2. The method for improving the stability of the catalyst in recycling HFC-23 according to claim 1, wherein the metal oxide is selected from the at least one metal oxide of Fe, Co, Ni or Zn in an amount of 0.5-2 wt %.

3. The method for improving the stability of the catalyst in recycling HFC-23 according to claim 1, wherein the decarbonization gas, HFC-23, and halogenated hydrocarbon form a mixed gas before introduction.

4. The method for improving the stability of the catalyst in recycling HFC-23 according to claim 1, wherein the decarbonization gas is a mixed gas of at least one of air, $Cl_2$, $CO_2$, or $O_2$ with $N_2$.

5. The method for improving the stability of the catalyst in recycling HFC-23 according to claim 1, wherein the halogenated hydrocarbon is chloroform or a mixture containing chloroform.

6. The method for improving the stability of the catalyst in recycling HFC-23 according to claim 5, wherein the main body catalyst is chromium, aluminum, or magnesium-based catalyst or chromium, aluminum, or magnesium catalyst supported on activated carbon/graphite.

7. The method for improving the stability of the catalyst in recycling HFC-23 according to claim 1, wherein conditions for the fluorine-chlorine exchange reaction are: a molar ratio of HFC-23 to halogenated hydrocarbon of 1:1-3, a reaction temperature of 250-400° C., a reaction pressure of 0.1-3 bar, and a residence time of 4-50 s.

8. The method for improving the stability of the catalyst in recycling HFC-23 according to claim 7, wherein the conditions for the fluorine-chlorine exchange reaction are: a molar ratio of HFC-23 to halogenated hydrocarbon of 1:1.2-2.2, a reaction temperature of 300-360° C., a reaction pressure of 1-2 bar, and a residence time of 4-12 s.

* * * * *